United States Patent [19]

Garcia et al.

[11] Patent Number: 5,082,858

[45] Date of Patent: Jan. 21, 1992

[54] NOVEL CHROMAN DERIVATIVES ACTIVE ON THE CENTRAL NERVOUS SYSTEM, THEIR METHOD OF PREPARATION AND PHARMACEUTICAL COMPOSITIONS IN WHICH THEY ARE PRESENT

[75] Inventors: Georges Garcia; Alain D. Malta, both of Saint-Gely-du-Fesc; Philippe Soubrie, St. Mathieu de Treviers, all of France

[73] Assignee: Sanofi, Paris, France

[21] Appl. No.: 440,090

[22] Filed: Nov. 22, 1989

[30] Foreign Application Priority Data

Nov. 23, 1988 [FR] France ............... 88 15284

[51] Int. Cl.⁵ .................. A61K 31/35; C07D 311/68
[52] U.S. Cl. ........................ 514/456; 549/404; 549/399; 549/220
[58] Field of Search ........... 549/399, 404, 220, 408; 514/456

[56] References Cited

U.S. PATENT DOCUMENTS

| | | | |
|---|---|---|---|
| 4,048,317 | 9/1977 | Wetts | 549/399 |
| 4,510,152 | 4/1985 | Faruk | 514/321 |

*Primary Examiner*—Nicky Chan
*Attorney, Agent, or Firm*—Bacon & Thomas

[57] ABSTRACT

Compounds of the formula

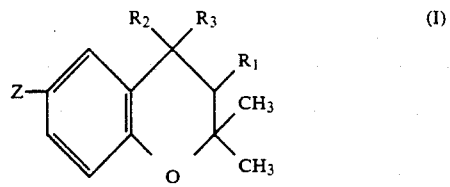

in which:

Z represents a halogen or a cyano, acetyl, trifluoroacetyl, nitro, $C_1$-$C_4$ alkylthio, carboxyl, phosphono, dialkoxyphosphonyl or alkoxycarbonyl group, the alkylthio and alkoxy groups containing from 1 to 3 carbon atoms;

$R_1$ denotes a hydroxyl group and $R_2$ represents hydrogen, or $R_1$ and $R_2$ taken together form an additional bond between the carbon atoms by which they are carried; and $R_3$ represents a group NH—X—$R_4$, in which X denotes a direct bond or an $SO_2$ group and $R_4$ represents a phenyl group which is unsubstituted or monosubstituted or disubstituted by a halogen, a nitro group, a $C_1$-$C_4$ group, a trifluoromethyl group, an amino group, a group —N(Alk)$_2$, a group —COOAlk or a group OAlk, Alk denoting a $C_1$-$C_4$ alkyl group;

a group —S—$R_5$, in which $R_5$ represents a $C_1$-$C_4$ alkyl group, a $C_3$-$C_7$ cycloalkyl or a phenyl group which is unsubstituted or monosubstituted or disubstituted by a halogen, a nitro group, a $C_1$-$C_4$ group, a trifluoromethyl group, an amino group, a group —N(Alk)$_2$, a group —COOAlk or a group AlOk, Alk denoting a $C_1$-$C_4$ alkyl group; or $R_5$ denotes a group —AlkN(Alk)$_2$ in which Alk is as defined above; or a group $SO_2R_5$, in which $R_5$ is as defined above, and the salts which the compounds of formula (I) are capable of producing with pharmaceutically acceptable acids when the substituent $R_3$ comprises an amino group.

6 Claims, No Drawings

NOVEL CHROMAN DERIVATIVES ACTIVE ON THE CENTRAL NERVOUS SYSTEM, THEIR METHOD OF PREPARATION AND PHARMACEUTICAL COMPOSITIONS IN WHICH THEY ARE PRESENT

The present invention relates to chroman and chromene derivatives having an activity on the central nervous system, especially as antidepressants.

Belgian patent 829 611 mentions a whole series of chroman-3-ol derivatives characterized by the presence of a group $—NR_1R_2$ in the 4-position, $R_1$ being hydrogen or a substituted or unsubstituted hydrocarbon group and $R_2$ representing hydrogen or an alkyl group, or the group $—NR_1R_2$ representing a heterocyclic group containing from 3 to 8 atoms which is unsubstituted or substituted by one or 2 methyl groups.

These derivatives may also carry a wide variety of substituents in the 6-position and 7-position.

The European patent application published under the number 76 075 describes chroman-3-ol derivatives characterized by the presence of a 2-oxopyrrolidin-1-yl group or a 2-oxopiperidino group in the 4-position and by the possible presence of a very wide variety of substituents in the 6-position or 7-position.

European patent application 93 535 describes chromene derivatives characterized by the presence of a 2-oxopiperidino or 2-oxopyrrolidin-1-yl group in the 4-position and by the possible presence of a wide variety of substituents in the 6-position or 7-position.

European patent application 273 262 describes a series of chroman-3-ol derivatives and chromene derivatives characterized by the presence, in the 4-position, of a 2-oxoheterocyclic group selected from pyridone, pyrazinone, pyridazinone, pyrimidinone and thiopyridone and from the corresponding partially hydrogenated rings, all these rings being substituted or unsubstituted. These chromanol and chromene derivatives are also unsubstituted or substituted in the 6-position or 7-position.

European patent application 296 975 describes chroman-3-ol derivatives which are also characterized by the presence of a 2-oxoheterocyclic group in the 4-position. Finally, European patent application 312 432 describes chromene derivatives substituted by a 2-oxopyrid-1-yl group in the 4-position.

All the compounds described in said patents or patent applications share a substantial activity on the cardiovascular system, especially as antihypertensives.

According to the present invention, it has now been found that, surprisingly, modifying the nature of the substituent in the 4-position gives compounds which have only a weak or zero activity on the cardiovascular system but which possess a very valuable activity on the central nervous system, especially as antidepressants.

The compounds according to the invention have the general formula

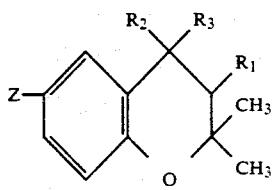

in which:
Z represents a halogen or a cyano, acetyl, trifluoroacetyl, nitro, $C_1$-$C_4$ alkylthio, carboxyl, phosphono, dialkoxyphosphonyl or alkoxycarbonyl group, the alkoxy group containing from 1 to 3 carbon atoms;

$R_1$ denotes a hydroxyl group and $R_2$ represents hydrogen, or $R_1$ and $R_2$ taken together form an additional bond between the carbon atoms by which they are carried; and $R_3$ represents
a group $NH—X—R_4$, in which X denotes a direct bond or an $SO_2$ group and $R_4$ represents a phenyl group which is unsubstituted or monosubstituted or disubstituted by a halogen, a nitro group, a $C_1$-$C_4$ alkyl group, a trifluoromethyl group, an amino group, a group $—N(Alk)_2$, a group $—COOAlk$ or a group $OAlk$, Alk denoting a $C_1$-$C_4$ alkyl group;

a group $—S—R_5$, in which $R_5$ represents a $C_1$-$C_4$ alkyl group, a $C_3$-$C_7$ cycloalkyl or a phenyl group which is unsubstituted or monosubstituted or disubstituted by a halogen, a nitro group, a $C_1$-$C_4$ alkyl group, a trifluoromethyl group, an amino group, a group $—N(Alk)_2$, a group $—COOAlk$ or a group $OAlk$, Alk denoting a $C_1$-$C_4$ alkyl group; or $R_5$ denotes a group $—AlkN(Alk)_2$, in which Alk is as defined above; or a group $SO_2R_5$, in which $R_5$ is as defined above, and the salts which the compounds of formula (I) are capable of producing with pharmaceutically acceptable acids when the substituent $R_3$ comprises an amine group.

In the present description and in the claims which follow, halogen will be understood as meaning a fluorine, chlorine or bromine atom.

The present invention further relates to a method of preparing the compounds of formula (I).

When $R_1$ represents a hydroxyl, the chroman-3-ols in which $R_3$ is a group $NHR_4$ or $SR_5$ are obtained by treating the epoxide of formula II:

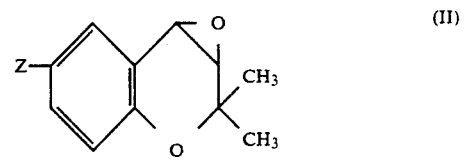

with the corresponding amine $R_4NH_2$ or thiol $R_5SH$.

The ring-opening reaction of the epoxide (II) is carried out at a temperature of between 10° and 100° C., in an inert organic solvent such as an alcohol, dioxane, tetrahydrofuran, methyl tert-butyl ether, dimethyl sulfoxide or dimethylformamide, in the presence of a basic condensation agent such as sodium hydride or a quaternary ammonium hydroxide like benzyltrimethylammonium hydroxide.

Under these operating conditions, ring opening of the epoxide (II) yields a chroman-3-ol derivative of trans configuration.

The starting epoxides (II) are known; they are described in particular in Belgian patent no. 852 955 and in European patent application 296 975.

When $R_3$ represents a group $—NHSO_2R_4$, it is not possible to open the epoxide ring with the corresponding sulfonamide. In this case, the corresponding compounds (I) are obtained from 4-amino-2,2-dimethyl-3- hydroxychroman derivatives (III) by substitution of the amino group with the sulfonyl chloride $R_4SO_2Cl$ according to the equation:

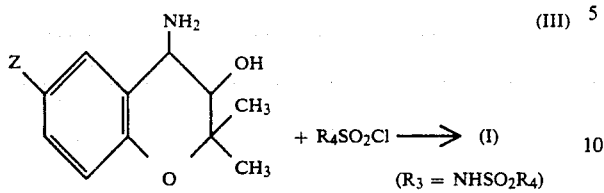

The reaction is carried out in a solvent, such as pyridine, which is capable of fixing the hydrochloric acid formed, at a temperature of between 20° and 50° C.

The amino derivatives (III) are known or are prepared according to the method described in particular in European patent application 76 075, by ring opening of the epoxide (II) with ammonia.

Finally, when $R_3$ represents a group $SO_2R_5$, the corresponding compounds (I) are obtained by oxidation, with hydrogen peroxide or an organic peracid, of the compounds (I) in which $R_3$ is a group $-SR_5$, which are prepared as indicated above. The reaction is carried out in conventional manner in an inert solvent such as chloroform, at a relatively low temperature (10° to 30° C.).

When $R_1$ and $R_2$ together represent a bond, the chromene derivatives of formula (I) are obtained by dehydration of the corresponding chroman-3-ols.

The dehydration is carried out with an alkali metal hydride such as sodium hydride, in an inert solvent such as tetrahydrofuran, at a temperature of between 50° and 100° C.

In the case where Z=CN, it is possible, according to a variant of the method, to start from a 3-bromo-6-cyano-4-hydroxychroman and treat it with an amine $NH_2R_4$ or a thiol $HSR_5$ (or an alkali metal salt thereof), in the presence of a condensation agent such as sodium hydride, in a solvent such as dimethyl sulfoxide.

Thus the following reactions are carried out in a single step:
 the in situ formation of the epoxide (II) from the starting bromohydrin,
 the opening of the epoxide ring with the amine or the thiol, and
 the dehydration of the resulting chroman-3-ol to give the chromene.

The non-limiting Examples which follow illustrate the preparation of the compounds of formula (I).

EXAMPLE 1

Trans-4-(4-chloroanilino)-6-cyano-2,2-dimethyl-3-hydroxychroman (SR 44546)

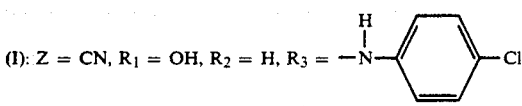

A solution of 3 g of 6-cyano-2,2-dimethyl-3,4-epoxychroman and 2.1 g of parachloroaniline in 50 ml of ethanol is refluxed for 72 hours.

The solvent is evaporated off under vacuum and the residue is taken up in ether. The solution is washed with water and dried and the solvent is evaporated off. The residue crystallizes from hexane. It is recrystallized from isopropyl ether.

Weight: 1 g M.p.: 125° C.

EXAMPLE 2

Trans-6-cyano-2,2-dimethyl-3-hydroxy-4-(2-methoxycarbonylanilino)chroman (SR 44588)

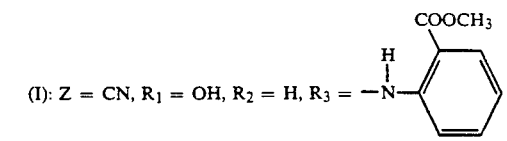

The procedure is the same as in Example 1, the parachloroaniline being replaced with an equivalent amount of methyl anthranilate and the heating time being limited to 18 hours. The expected product is obtained in the same manner.

M.p.: 164° C.

EXAMPLE 3

Trans-6-cyano-2,2-dimethyl-3-hydroxy-4-(2-trifluoromethylbenzene-1-sulfonamido)chroman (SR 44665)

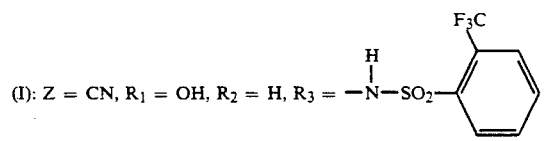

A mixture of 1 g of 4-amino-6-cyano-2,2-dimethyl-3-hydroxychroman and 1 g of 2-trifluoromethylbenzenesulfonyl chloride in 25 ml of pyridine is stirred at room temperature for 18 hours.

The pyridine is evaporated off and the residue is taken up in methylene chloride. The organic solution is washed with a dilute solution of hydrochloric acid and then dried over sodium sulfate and the solvent is removed under vacuum.

The solid residue is recrystallized from an isopropyl ether/isopropanol mixture.

Weight: 0.9 g M.p.: 211°-212° C.

EXAMPLE 4

Trans-6-cyano-2,2-dimethyl-4-(N,N-dimethylsulfamoylamino)-3-hydroxychroman (SR 44666)

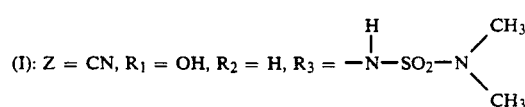

The procedure is the same as in Example 3, the 2-trifluoromethylbenzenesulfonyl chloride being replaced with an equivalent amount of N,N-dimethylsulfamoyl chloride.

M.p.: 172°-173° C. (isopropyl ether).

EXAMPLE 5

Trans-4-(4-chlorophenylthio)-6-cyano-2,2-dimethyl-3-hydroxychroman (SR 44611)

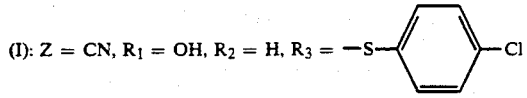

(I): Z = CN, R$_1$ = OH, R$_2$ = H, R$_3$ = —S—⟨⟩—Cl

A mixture of 2 g of 6-cyano-2,2-dimethyl-3,4-epoxychroman and 1.8 g of parachlorothiophenol in 15 ml of dioxane and 0.3 ml of a 35% methanolic solution of benzyltrimethylammonium hydroxide is refluxed for 5 hours.

The solvent is evaporated off under vacuum and the residue is taken up in pentane. After crystallization, the product is recrystallized from isopropyl ether.

M.p.: 143° C.

EXAMPLE 6

Trans-6-cyano-2,2-dimethyl-4-(2-dimethylaminoethylthio)-3-hydroxychroman hydrochloride (SR 44652 A)

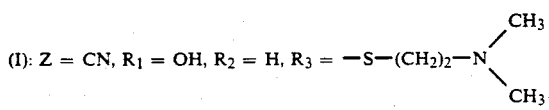

(I): Z = CN, R$_1$ = OH, R$_2$ = H, R$_3$ = —S—(CH$_2$)$_2$—N(CH$_3$)$_2$

A mixture of 2 g of 6-cyano-2,2-dimethyl-3,4-epoxychroman and 3 g of 2-dimethylaminoethanethiol hydrochloride in 15 ml of ethanol and 12 ml of a 35% methanolic solution of benzyltrimethylammonium hydroxide is refluxed for 2 hours.

The solvents are evaporated off under vacuum and the residue is taken up in 30 ml of water and then extracted with ether. The ether solution is dried over sodium sulfate and the solvent is evaporated off under vacuum.

This gives an oil (4 g), which is dissolved in 8 ml of ethanol. 1.45 ml of concentrated hydrochloric acid and then 60 ml of ether are added.

A colorless solid (4 g) is obtained.

M.p.: 169° C. Crystallized with 0.5 molecule of water.

EXAMPLE 7

4-(4-Chlorophenylthio)-6-cyano-2,2-dimethyl-2H-chromene (SR 44554)

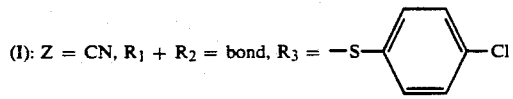

(I): Z = CN, R$_1$ + R$_2$ = bond, R$_3$ = —S—⟨⟩—Cl

A mixture of 7 g of 3-bromo-6-cyano-2,2-dimethyl-4-hydroxychroman and 30 ml of dimethyl sulfoxide is stirred at 15° C. 0.6 g of sodium hydride is added and stirring is continued at 15° C. for 1 hour.

4.6 g of sodium parachlorothiophenate are added and the mixture is stirred for 20 hours at 20° C. The reaction mixture is poured on to 150 g of ice and extracted with ether. The organic solution is washed with a 1N solution of sodium hydroxide and then with a 1N solution of hydrochloric acid.

The solution is dried over sodium sulfate and the solvent is evaporated off under vacuum. The oily residue crystallizes. It is recrystallized once from isopropyl ether and a second time from isopropanol. Colorless crystals are obtained.

M.p.: 117° C.

EXAMPLE 8

Trans-6-cyano-4-cyclohexylsulfonyl-2,2-dimethyl-3-hydroxychroman (SR 44708)

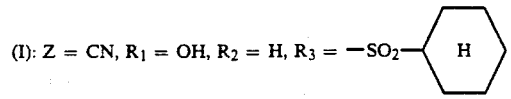

(I): Z = CN, R$_1$ = OH, R$_2$ = H, R$_3$ = —SO$_2$—⟨H⟩

A)

Trans-6-cyano-4-cyclohexylthio-2,2-dimethyl-3-hydroxychroman

A mixture of 1.5 g of 6-cyano-2,2-dimethyl-3,4-epoxychroman, 1.2 g of cyclohexylmercaptan and 0.3 g of a 35% methanolic solution of benzyltrimethylammonium hydroxide in 10 ml of tetrahydrofuran is refluxed for 8 hours.

It is evaporated to dryness under vacuum and the residue is taken up in 50 ml of ether. The solution is washed with water and dried over sodium sulfate and the solvent is evaporated off. An oil remains, which is taken up in 50 ml of boiling pentane. Colorless crystals are obtained on cooling to 0° C.

M.p.: 101° C.

B) SR 44708

A mixture of 1.2 g of the product prepared above and 4.8 g of metachloroperbenzoic acid in 50 ml of chloroform is kept at 20° C. for 2 hours.

100 ml of methylene chloride are added and the organic solution is washed with a 10% solution of sodium carbonate and then with water. The solution is dried and the solvents are evaporated off under vacuum to give a solid, which is recrystallized from absolute ethanol.

M.p.: 202° C.

EXAMPLES 9 TO 23

The compounds according to the invention which are described in Table I below were prepared by following the procedure of Example 1:

TABLE I

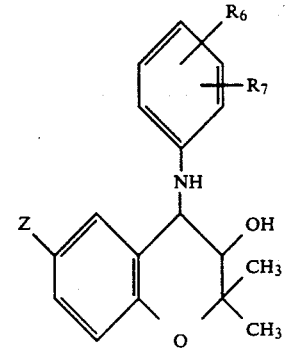

| Compound SR no. (Example) | Z | R$_6$ | R$_7$ | Melting point (solvent) |
|---|---|---|---|---|
| SR 46063 (9) | NO$_2$ | H | 4-Cl | M.p. = 183° C. ((iPr$_2$O)) |
| SR 46142 A (10) | CN | H | H | hydrochloride M.p. = 185° C. |

TABLE I-continued

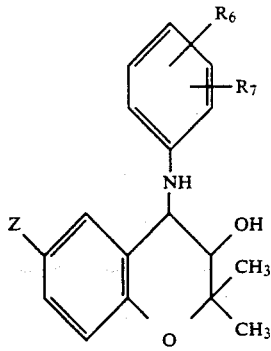

| Compound SR no. (Example) | Z | R6 | R7 | Melting point (solvent) |
|---|---|---|---|---|
| SR 46143 (11) | CN | H | 4-F | M.p. = 125° C. (acetonitrile) ((iPr)2O) |
| SR 46144 (12) | CN | H | 3-Cl | M.p. = 155° C. ((iPr)2O) |
| SR 46145 (13) | CN | H | 4-CH3 | M.p. = 111° C. ((iPr)2O) |
| SR 46146 (14) | CN | H | 4-OCH3 | M.p. = 173° C. (AcOEt) |
| SR 46276 (15) | CN | H | 4-CF3 | NMR |
| SR 46344 (16) | NO2 | H | 3-Cl | M.p. = 170° C. |
| SR 46357 (17) | CN | H | 3-F | M.p. = 128° C. ((iPr)2O) |
| SR 46358 (18) | CN | H | 3-Br | hemihydrate M.p. = 160–163° C. |
| SR 46462 (19) | CN | 2-Cl | 4-Cl | M.p. = 168° C. ((iPr)2O/hexane) |
| SR 46463 (20) | CN | 3-Cl | 4-CH3 | M.p. = 163° C. ((iPr)2O/hexane) |
| SR 46482 (21) | CN | H | 3-NO2 | M.p. = 163–165° C. ((iPr)2O/hexane) |
| SR 46483 (22) | CN | H | 3-NH2 | M.p. = 173° C. ((iPr)2O/hexane) |
| SR 46568 (23) | CN | H | 3-N(CH3)2 | M.p. = 77–79° C. (hexane) |

The following abbreviations have been used for the recrystallization solvents:
(iPr)2O: isopropyl ether
AcOEt: ethyl acetate The compound SR 46276 was characterized by its NMR spectrum.

The products according to the invention were studied for their therapeutic activity.

Thus the products according to the invention were subjected to the forced swimming test according to Porsolt et al. (Archives Internationales de Pharmacodynamie, 1977, 229, 327–336).

Female mice (Iffa Credo) weighing 22–24 g are immersed for a period of 6 minutes in a beaker containing 800 ml of water at 24°±1° C.

The immobility times are measured over 4 minutes from the 2nd to the 6th minute.

The results are expressed as the percentage inhibition of the immobility times of the treated animals compared with the control animals.

The results obtained with various products according to the invention are indicated in Table II below.

TABLE II

| Product | Dose mg/kg i.p. | % inhibition |
|---|---|---|
| SR 44546 | 0.06 | 16 |
| | 0.25 | 44 |
| SR 44588 | 0.06 | 20 |
| | 0.125 | 27 |
| SR 44665 | 0.06 | 24 |
| | | 34 |
| SR 44666 | 0.06 | 21 |
| | 1 | 23 |
| SR 44652 | 0.06 | 25 |
| | 0.125 | 27 |
| SR 44554 | 0.06 | 33 |
| SR 44708 | 0.06 | 21 |
| | 0.25 | 37 |
| SR 46142 A | 0.06 | 40 |
| SR 46143 | 0.06 | 27 |
| SR 46276 | 0.06 | 40 |

These results show that the products tested possess antidepressant properties at low doses.

Furthermore, the products according to the invention were studied for their cardiovascular properties and especially their antihypertensive properties. In spontaneously hypertensive rats, the products showed no activity, even at doses very much greater than those at which they are active on the central nervous system.

Finally, the products according to the invention show no signs of toxicity at the doses at which they are active.

The products according to the invention can therefore be used in medicine as drugs active on the central nervous system.

According to a second aspect, the present invention relates to pharmaceutical compositions containing an effective dose of a compound of formula (I) with suitable excipients.

The excipients used are chosen according to the pharmaceutical form and the desired mode of administration.

In the pharmaceutical compositions of the present invention for oral, sublingual, subcutaneous, intramuscular, intravenous or rectal administration, the active principles of formula (I) above, or salts thereof if desired, can be administered to humans in unit forms of administration, mixed with conventional pharmaceutical excipients, for the prophylaxis or treatment of the above disorders or diseases. The appropriate unit forms of administration include forms for oral administration, such as tablets, capsules, powders, granules and solutions or suspensions to be taken orally, forms for buccal administration, forms for subcutaneous, intramuscular or intravenous administration and forms for rectal administration.

To obtain the desired prophylactic or therapeutic effect, the dose of active principle can vary between 0.5 and 25 mg per kg of body weight per day.

Each unit dose can contain from 10 to 500 mg, preferably from 25 to 300 mg, of active ingredients in combination with a pharmaceutical excipient. This unit dose can be administered 1 to 5 times a day so as to administer a daily dosage of 25 to 3000 mg, preferably 50 to 1500 mg.

When a solid composition is prepared in the form of tablets, the principal active ingredient is mixed with a pharmaceutical vehicle such as gelatin, starch, lactose, magnesium stearate, talc, gum arabic or the like. The tablets can be coated with sucrose, a cellulose derivative or other appropriate substances, or they can be treated in such a way that they have a sustained or delayed activity and release a predetermined amount of active principle continuously.

A preparation in the form of capsules is obtained by mixing the active ingredient with a diluent and pouring the resulting mixture into soft or hard capsules.

A preparation in the form of a syrup or an elixir or for administration in the form of drops may contain the active ingredient in combination with a sweetener, which is preferably calorie-free, methylparaben and propylparaben as antiseptics, a flavoring agent and an appropriate dye.

Water-dispersible granules or powders may contain the active ingredient mixed with dispersants, wetting agents or suspension agents, such as polyvinylpyrrolidone, as well as with sweeteners or taste correctors.

Rectal administration is carried out using suppositories, which are prepared with binders melting at the rectal temperature, for example cacao butter or polyethylene glycols.

Parenteral administration is carried out using aqueous suspensions, isotonic saline solutions or sterile and injectable solutions which contain pharmacologically compatible dispersants and/or wetting agents, for example propylene glycol or butylene glycol.

The active principle may also be formulated as microcapsules, with one or more excipients or additives if desired.

As an example of a pharmaceutical preparation, it is possible to prepare gelatin capsules containing:
SR 44546—0.050 g
Lactose—0.100 g
Magnesium stearate—0.025 g
by intimately mixing the above ingredients and pouring the mixture into hard gelatin capsules.

What is claimed is:

1. A compound of the formula

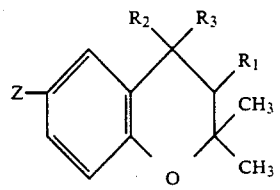

in which:

Z represents a halogen or a cyano, acetyl, trifluoroacetyl, nitro, $C_1$-$C_4$ alkylthio, carboxyl, phosphono, dialkoxyphosphonyl or alkoxycarbonyl group, the alkylthio and alkoxy groups containing from 1 to 3 carbon atoms;

$R_1$ denotes a hydroxyl group and $R_2$ represents hydrogen, or $R_1$ and $R_2$ taken together form an additional bond between the carbon atoms by which they are carried; and $R_3$ represents
a group NH—X—$R_4$, in which X denotes a direct bond and $R_4$ represents a phenyl group which is monosubstituted or disubstituted by a halogen, a nitro group, a trifluoromethyl group, an amino group, a group —N(Alk)$_2$, or a group —COOAlk with Alk denoting a $C_1$-$C_4$ alkyl group;

or a pharmaceutically acceptable salt thereof.

2. A compound as claimed in claim 1, wherein Z is cyano or nitro.

3. A compound as claimed in claim 2, wherein $R_3$ represents
a group NH—X—$R_4$, in which X denotes a direct bond and $R_4$ represents a phenyl group which is monosubstituted or disubstituted by a halogen.

4. A compound as claimed in claim 2, wherein $R_3$ represents
a group NH—X—$R_4$, in which X denotes a direct bond and $R_4$ represents a phenyl group which is monosubstituted by a halogen, a nitro group, a trifluoromethyl group, an amino group, a group —N(Alk)$_2$, or a group —COOAlk with Alk denoting a $C_1$-$C_4$ alkyl group.

5. Trans-4-(4-chloroanilino)-6-cyano-2,2-dimethyl-3-hydroxychroman.

6. An antidepressant pharmaceutical composition having weak or no activity on the cardiovascular system containing a compound of claim 5 in admixture with a pharmaceutically acceptable excipient.

* * * * *